(12) United States Patent
Schemmer et al.

(10) Patent No.: US 7,021,930 B2
(45) Date of Patent: Apr. 4, 2006

(54) OZONE APPLICATOR CUP

(76) Inventors: Jurgen H. Schemmer, 2725 Lloyd Town, Aurora, Road., King City, Ontario (CA) L7B 1A3; Patrick Knapp, deceased, late of Adams, MA (US); by Susan Knapp, legal representative, 78 East St., Adams, MA (US) 01200

( * ) Notice: Subject to any disclaimer, the term of this patent is extended or adjusted under 35 U.S.C. 154(b) by 105 days.

(21) Appl. No.: 10/610,113

(22) Filed: Jun. 30, 2003

(65) Prior Publication Data
US 2004/0137402 A1 Jul. 15, 2004

Related U.S. Application Data

(60) Provisional application No. 60/393,206, filed on Jul. 2, 2002.

(51) Int. Cl.
*A61C 17/02* (2006.01)

(52) U.S. Cl. .......................................... 433/80; 433/88
(58) Field of Classification Search ................. 433/80, 433/88, 116
See application file for complete search history.

(56) References Cited

U.S. PATENT DOCUMENTS

| | | | | |
|---|---|---|---|---|
| 4,692,140 A * | 9/1987 | Olson | ............................ | 604/40 |
| 5,120,219 A * | 6/1992 | De Farcy | ...................... | 433/88 |
| 5,145,367 A * | 9/1992 | Kasten | .......................... | 433/84 |
| 5,197,876 A * | 3/1993 | Coston | ........................ | 433/116 |
| 5,547,376 A * | 8/1996 | Harrel | .......................... | 433/116 |
| 5,890,898 A * | 4/1999 | Wada et al. | ................. | 433/116 |
| 6,155,824 A * | 12/2000 | Kamen et al. | ................ | 433/80 |
| 6,186,783 B1* | 2/2001 | Brassil et al. | ................. | 433/91 |
| 6,454,566 B1* | 9/2002 | Lynch et al. | ................... | 433/80 |
| 6,743,016 B1* | 6/2004 | Lynch et al. | ................... | 433/80 |

* cited by examiner

*Primary Examiner*—Ralph A. Lewis
(74) *Attorney, Agent, or Firm*—Phillips Lytle LLP

(57) ABSTRACT

A cup for use with the handpiece of an apparatus for applying gas to a portion of a tooth comprising a liner (18) configured and arranged to engage a gas dispensing handpiece, a body (16) defining a gas exposure chamber (28), the body having a higher resiliency to deformation than the liner. The body may be so deformable that it forms against the surface of a tooth to effect a seal and to expose a portion of the tooth to gas circulated in the chamber. The body may overmold the liner and may be formed of thermal-plastic rubber, and the liner may be formed of a plastic material. The gas exposure chamber may be cylindrical.

5 Claims, 3 Drawing Sheets

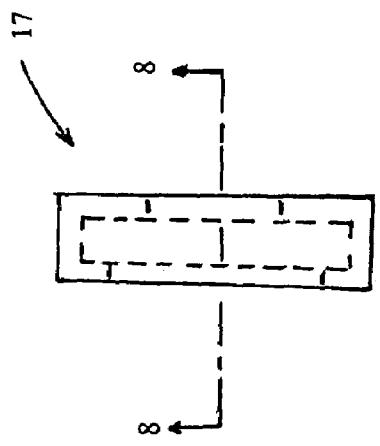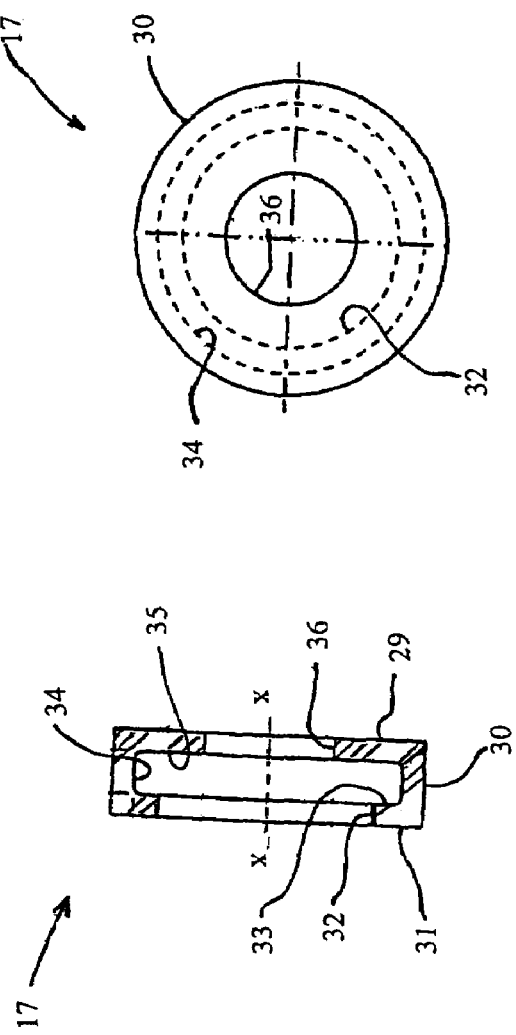

OZONE APPLICATOR CUP

This application claims the benefit of U.S. Provisional Application(s) No. 60/393,206 filing date Jul. 2, 2002

TECHNICAL FIELD

The present invention relates to apparatus for applying ozone in the treatment of dental caries and, more particularly, to an improved cup for the handpiece of an apparatus for treating dental caries.

BACKGROUND ART

The use of ozone in the treatment of dental caries is shown and described in U.S. patent application Ser. No. 09/712,611, which issued Sep. 24, 2002 as U.S. Pat. No. 6,454,566 entitled "Apparatus for the Treatment of Dental Caries." U.S. Pat. No. 6,454,566 in its entirety, including the specification and drawings, is incorporated herein by reference. That patent discloses an apparatus for the treatment of dental caries which generally includes a source of oxidizing gas and a handpiece for delivering the gas to a tooth. A cup attached to the handpiece is provided for receiving the gas and exposing a selected area of the tooth to the gas. Such cup is a unitary formed member which includes a resilient edge for sealably engaging the tooth around the selected area to prevent escape of the gas therepast. All of the disclosed embodiments of the cups include cup chambers that subtend cup edges. The cups include walls that define the chamber and include first perimeters for sealably coupling the walls to the handpiece and second perimeters that provide for coupling the walls to the tooth and exposing the selected areas to gas circulated in the chambers.

However, it has been found that the cups taught in the prior art do not adequately provide both a secure but temporary attachment to the outlet of the handpiece as well as proper resiliency with respect to the portion of the cup applied to the tooth. Accordingly, it would be useful to provide a cup for use with the handpiece which provides the proper rigidity desired to fit tightly around the outlet of the ozone dispensing handpiece as well as the flexibility desired for the cup to form around an uneven tooth to affect a vacuum seal before the unit dispenses ozone.

DISCLOSURE OF THE INVENTION

With parenthetical reference to the corresponding parts, portions or surfaces of the disclosed embodiment, merely for the purposes of illustration and not by way of limitation, the present invention provides an improved cup (15) for use with the handpiece of an apparatus for applying ozone to the surface of a tooth. The improvement comprises a liner (17) configured and arranged to engage a gas dispensing handpiece, a body (16) defining a gas exposure chamber (28), the liner having a higher resiliency to deformation than the body. The body may be so deformable that it forms against the surface of a tooth to effect a seal and to expose a portion of the tooth to gas circulated in the chamber. The body may overmold the liner and may be formed of thermal-plastic rubber, and the liner may be formed of a plastic material. The gas exposure chamber may be cylindrical. The present invention also discloses a method for manufacturing the improved cup.

Accordingly, the general object of the present invention is to provide an improved cup which fits properly onto the handpiece of an ozone dispensing device.

Another object is to provide an improved cup which is flexible or pliable enough for the edge of the cup to form against the uneven surfaces of a tooth to affect a vacuum seal.

Another object is to provide an improved cup which is rigid enough to removably attach to the outlet of a handpiece.

Another object is to provide an improved cup which is disposable.

Another object is to provide an improved cup having a liner and an over molded body.

Another object is to provide an improved method for manufacturing a cup.

Another object is to provide an improved method of manufacturing a cup in which the liner is insert molded with the body being formed around it.

These and other objects and advantages will become apparent from the foregoing and ongoing written specification and the drawings.

BRIEF DESCRIPTION OF THE DRAWINGS

FIG. 7 is a rotated front view of the liner shown in FIG. 1.

FIG. 8 is a horizontal sectional view of the liner shown in FIG. 7, taken generally on line 8—8 of FIG. 7.

FIG. 9 is a right side view of the liner shown in FIG. 7.

DESCRIPTION OF THE PREFERRED EMBODIMENTS

Figure 3:
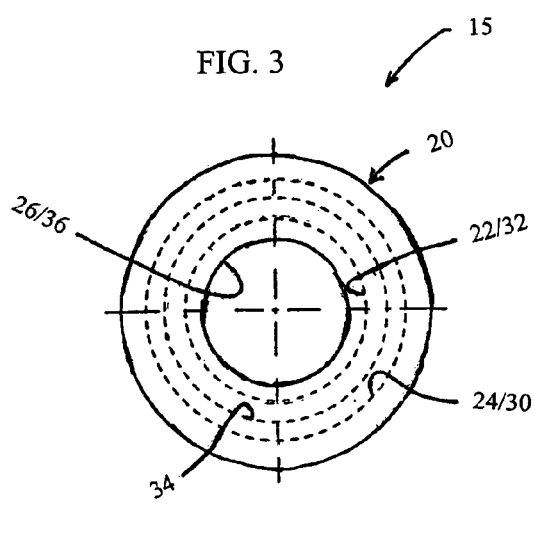
FIG. 3 is a plan view of the cup shown in FIG. 1.

At the outset, it should be clearly understood that like reference numerals are intended to identify the same structural elements, portions or surfaces, consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

Figure 2:
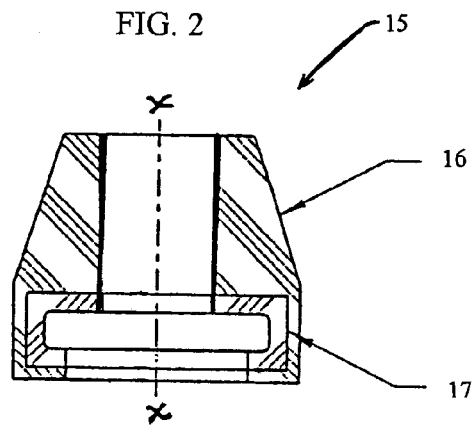
FIG. 2 is a vertical sectional view of the cup shown in FIG. 1, taken generally on line 2—2 of FIG. 1.
Figure 1:
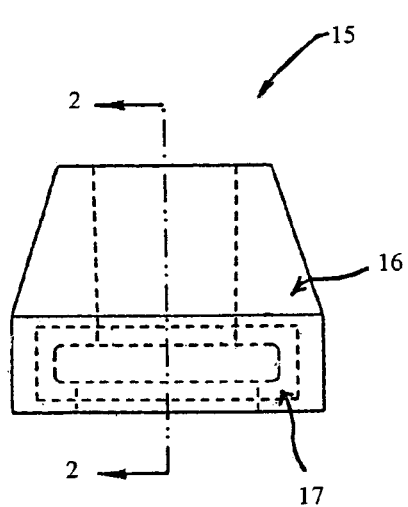
FIG. 1 is a front view of the improved cup.

Referring now to the drawings and, more particularly, to FIGS. 1 and 2 thereof, this invention provides an improved ozone applicator cup, of which the presently preferred embodiment is generally indicated at 15. Cup 15 is shown as broadly including a body 16 and a liner 17. Body 16 and liner 17 are generally cylindrically shaped members.

Figure 4:
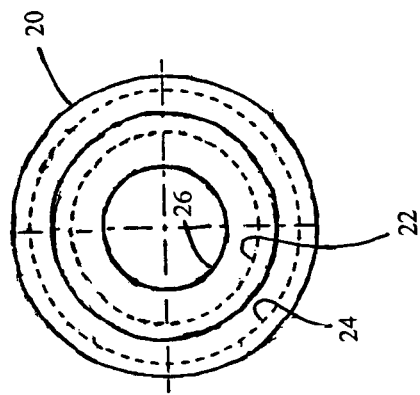
FIG. 4 is a rotated front view of the body shown in FIG. 1.
Figure 5:
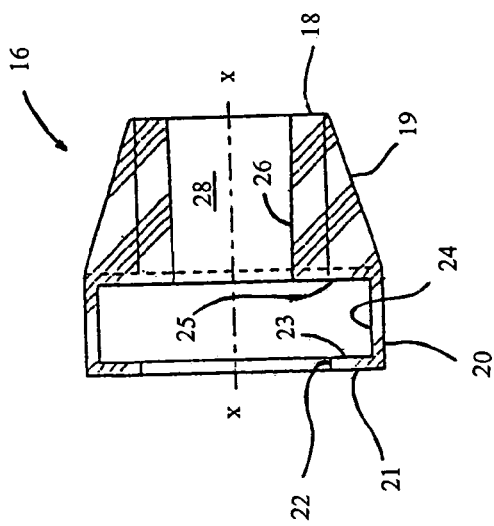
FIG. 5 is a horizontal sectional view of the body shown in FIG. 4, taken generally on line 5—5 of FIG. 4.

FIG. 4 shows body 16 of cup 15. FIG. 5 is a sectional view of body 16 shown in FIG. 4, taking generally on line 5—5 of FIG. 4. Referring to FIG. 5, body 16 is a specially configured member elongated along axis x—x and is bounded by a rightwardly-facing annular vertical surface 18, a rightwardly and outwardly-facing frusto-conical surface 19, an outwardly-facing horizontal cylindrical surface 20, a leftwardly-facing annular vertical surface 21, an inwardly-facing horizontal cylindrical surface 22, a rightwardly-facing annular vertical surface 23, an inwardly-facing horizontal cylindrical surface 24, a leftwardly-facing annular vertical surface 25, and an inwardly-facing horizontal cylindrical surface 26, joined at its right marginal end to the inner marginal end of surface 18. Surface 26 generally defines cup chamber 28.

Figure 6:
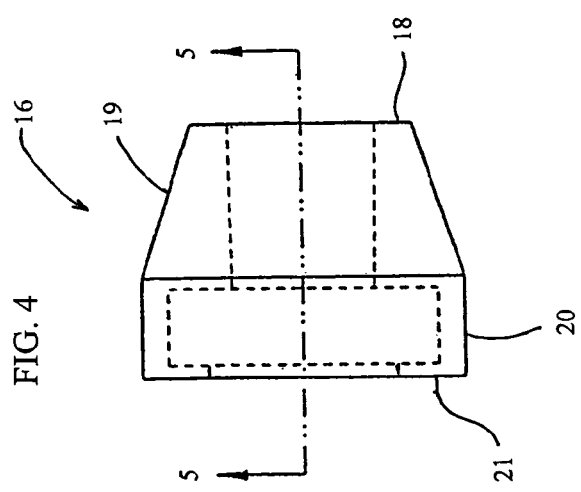
FIG. 6 is a right side view of the body shown in FIG. 5.

FIG. 6 shows liner 17 of cup 15. FIG. 8 is a sectional view of liner 17, taken generally on line 8—8 of FIG. 7. Referring to FIG. 8, liner 17 is a specially-configured solid member elongated along axis x—x, and is bounded by a rightwardly-facing annular vertical surface 29, an outwardly-facing horizontal cylindrical surface 30, a leftwardly-facing annular vertical surface 31, an inwardly-facing horizontal cylindrical surface 32, a rightwardly-facing annular vertical surface 33, an inwardly-facing horizontal cylindrical surface 34, a leftwardly-facing annular vertical surface 35, and an inwardly-facing horizontal cylindrical surface 36, joined at its right marginal end to the inner marginal end of surface 29.

As shown in FIGS. 1–2, liner 17 is encased in the bottom portion of body 16. In particular, liner 17 fits within the recess defined by surfaces 23, 24 and 25 of body 16. Thus, surface 29 of liner 17 abuts surface 25 of body 16, surface 30 of liner 17 abuts surface 24 of body 16, and surface 31 of liner 17 abuts surface 23 of body 16. Thus, when fully formed, the diameter of cylindrical surface 32 and the diameter of cylindrical surface 22 are the same. Also, the diameter of cylindrical surface 36 is approximately the same as the diameter of the cylindrical surface 26.

Cup 15 is manufactured using a two-part molding process in a controlled and clean environmental. The first step of the process is to form liner 17. Liner 17 is formed by conventional injection molding. The injection mold is a 32-cavity, hot runner SPI 102 production mold. Thus, each cycle produces 32 liners and the plastic remains molten right up to injection into the part. SPI refers to the Society of Plastics Industry, Inc. classifications. A Class 102 mold generally has a cycle life of less than one million cycles and a minimum base hardness of 280 BHN. The material used to form liner 17 is a plastic material. It has a good abrasion resistance and overmold adhesion to polypropylene and good compression set. In the preferred-embodiment, it has the following characteristics:

| | |
|---|---|
| SPECIFIC GRAVITY ref. ASTM D792, 23/23° C. | 0.89 |
| SHORE A HARDNESS ref. ASTM D2240, 10 sec. | 68 |
| TENSILE STRENGTH (PSI) ref. ASTM D412-Die C, 2 hrs, 23° C. | 952 |
| ELONGATION (%) ref. ASTM D412-Die C, 2 hrs, 23° C. | 639 |
| MODULUS @ 300% (PSI) ref. ASTM D412-Die C, 2 hrs, 23° C. | 551 |
| VISCOSITY @ 11170/sec (Pa-sec) 200° C. | 6.4 |

As a result, it will not unduly deform when fit onto the outlet of a handpiece for an ozone delivery device. The VERSALLOY XL 9070X-1 product sold by GLS Corporation, of 833 Ridgeview Dr., McHenry, Ill. 60050 may be employed in the preferred embodiment.

The second step is the overmold of body 16. Liner 17 is insert molded with body 16 being formed over it (overmolded). In the preferred embodiment, the injection mold is a 16-cavity, hot runner SPI 102 production mold with interchangeable 16-cavity sets for each of the desired sizes. A snap core pin protrudes up from the bottom of the cavity to simulate the outlet of the handpiece and has the same features as the particular handpiece with which the cup will be used. The liner is positioned on the pin and then overmolded with body 16. Using this type of overmolding, the physical characteristics of liner 17 and body 16 can be different. Accordingly, liner 17 is designed with features, such as higher resiliency to deformation, to allow for an appropriate fit of cup 15 onto a handpiece, while body 16 is designed with features, such as higher pliability and softness, to allow for cup 15 to create a seal around a tooth surface to expose the subject area to gas circulated in chamber 28. The material used to form overmolded body 16 is a thermoplastic rubber compound. In the preferred embodiment, it has the following characteristics:

| | |
|---|---|
| SPECIFIC GRAVITY ref. ASTM D792, 23/23° C. | 0.86 |
| SHORE A HARDNESS ref. ASTM D2240, 10 sec. | 3 |
| TENSILE STRENGTH (PSI) ref. ASTM D412-Die C, 2 hrs, 23° C. | 300 |
| ELONGATION (%) ref. ASTM D412-Die C, 2 hrs, 23° C. | 1,516 |
| MODULUS @ 300% (PSI) ref. ASTM D412-Die C, 2 hrs, 23° C. | 25 |
| VISCOSITY @ 11170/sec (Pa-sec) 200° C. | 2.3 |
| COLOR | Clear |

The VERSAFLEX CL2000X compound sold by GLS Corporation, of 833 Ridgeview Dr., McHenry, Ill. 60050 may be employed in the preferred embodiment.

With respect to both liner 17 and body 16, a color concentrate may be added, with different colors identifying different part sizes.

The present invention contemplates that many changes and modifications may be made. For example, the particular dimensions of the preferred embodiment may be altered as may be the cross-sectional geometry. For example, body 16 and liner 17 may have an oval geometry rather than a cylindrical geometry, or surface 26 may be tapered with a leftwardly and inwardly-facing frusto-conical surface. Therefore, while the presently-preferred form of the cup has been shown and described, and several modifications thereof discussed, persons skilled in this art will readily appreciate that various additional changes and modifications made be made without departing from the spirit of the invention.

What is claimed is:

1. An ozone delivery system comprising:

an ozone delivery device;

a gas dispensing handpiece in communication with said ozone delivery device;

a cup engaging said gas dispensing handpiece;

said cup having a liner configured to engage said gas dispensing handpiece and a body defining a gas exposure chamber;

said body encasing said liner and said liner having a higher resiliency to deformation then said body.

2. The ozone delivery system set forth in claim 1, wherein said cup body is configured to form against the surface of a tooth to effect a seal and to expose a portion of said tooth to gas circulated in said chamber.

3. The ozone delivery system set forth in claim 1, wherein said cup body is formed of thermal-plastic rubber.

4. The ozone delivery system set forth in claim 1, wherein said cup liner is formed of a plastic material.

5. The ozone delivery system set forth in claim 1, wherein said cup chamber is cylindrical.

* * * * *